(12) United States Patent
Wentland

(10) Patent No.: US 8,642,615 B2
(45) Date of Patent: *Feb. 4, 2014

(54) METHODS OF USING 8-CARBOXAMIDO-2,6-METHANO-3-BENZAZOCINES

(75) Inventor: Mark P. Wentland, Watervliet, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/556,650

(22) Filed: Jul. 24, 2012

(65) Prior Publication Data

US 2012/0302591 A1    Nov. 29, 2012

Related U.S. Application Data

(60) Division of application No. 13/103,599, filed on May 9, 2011, now Pat. No. 8,252,929, which is a continuation of application No. 12/249,238, filed on Oct. 10, 2008, now Pat. No. 7,956,187, which is a division of application No. 11/205,354, filed on Aug. 17, 2005, now abandoned, which is a division of application No. 10/987,527, filed on Nov. 12, 2004, now Pat. No. 7,265,226, which is a division of application No. 10/409,803, filed on Apr. 9, 2003, now Pat. No. 6,887,998, which is a division of application No. 10/305,287, filed on Nov. 26, 2002, now Pat. No. 6,784,187, which is a continuation-in-part of application No. PCT/US01/45581, filed on Oct. 31, 2001.

(60) Provisional application No. 60/244,438, filed on Oct. 31, 2000.

(51) Int. Cl.
*A61K 31/485* (2006.01)
*A61K 31/4748* (2006.01)

(52) U.S. Cl.
USPC ............................ 514/282; 514/279; 514/295

(58) Field of Classification Search
USPC .......................................... 514/279, 282, 295
See application file for complete search history.

(56) References Cited

U.S. PATENT DOCUMENTS

| | | | |
|---|---|---|---|
| 3,856,795 A | 12/1974 | Yardley | |
| 3,957,793 A | 5/1976 | Wentland et al. | |
| 4,032,529 A | 6/1977 | Wentland et al. | |
| 4,205,171 A | 5/1980 | Albertson | |
| 4,374,139 A | 2/1983 | Mohacsi | |
| 4,464,378 A | 8/1984 | Hussain | |
| 4,649,200 A | 3/1987 | Portoghese | |
| 5,258,386 A | 11/1993 | Newman | |
| 5,607,917 A | 3/1997 | Carter et al. | |
| 6,365,594 B1 | 4/2002 | Dondio et al. | |
| 6,784,187 B2 | 8/2004 | Wentland | |
| 6,812,236 B2 | 11/2004 | Gibson et al. | |
| 6,887,998 B2 | 5/2005 | Wentland | |
| 7,262,298 B2 | 8/2007 | Wentland | |
| 7,265,226 B2 | 9/2007 | Wentland | |
| 7,557,119 B2 | 7/2009 | Wentland | |
| 7,956,187 B2 | 6/2011 | Wentland | |
| 8,252,929 B2 | 8/2012 | Wentland | |
| 2002/0099216 A1 | 7/2002 | Gibson et al. | |
| 2006/0030580 A1 | 2/2006 | Wentland | |

FOREIGN PATENT DOCUMENTS

| | | |
|---|---|---|
| EP | 0254120 | 1/1988 |
| EP | 0632041 | 1/1995 |
| GB | 1340720 | 12/1998 |
| WO | WO 93/11761 | 6/1993 |
| WO | WO 97/25331 | 7/1997 |
| WO | WO 98/52929 | 11/1998 |
| WO | WO 02/36573 | 5/2002 |
| WO | WO 03/101963 | 12/2003 |

OTHER PUBLICATIONS

Wentland et al., "3-Carboxamido Analogues of Morphine and Naltrexone: Synthesis . . . ", Bioorg. Med. Chem. Ltrs. 11, pp. 1717-1721 (2001).

Wentland et al., "8-Carboxamidocyclazocine Analogues: Redefining the Structure-Activity . . .", Bioorg. Med. Chem. Ltrs 11, pp. 623-626 (2001).

(Continued)

*Primary Examiner* — Charanjit Aulakh
(74) *Attorney, Agent, or Firm* — Heslin Rothenberg Farley & Mesiti P.C.

(57) ABSTRACT

8-Substituted-2,6-methano-3-benzazocines of general structure I in which A is —$CH_2$—OH, —$CH_2NH_2$, —$NHSO_2CH_3$,

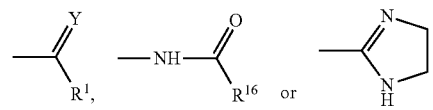

and Y is O, S or NOH are useful as analgesics, anti-diarrheal agents, anticonvulsants, antitussives and anti-addiction medications.

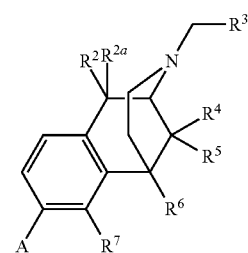

8-Carboxamides, thiocarboxamides, hydroxyamidines and formamides are preferred.

17 Claims, No Drawings

(56) References Cited

OTHER PUBLICATIONS

Davies et al., "Palladium catalysed elaboration of codeine and morphine", J. Chem. Soc, Pekin Trans. 1, pp. 1413-1420 (2000).
McCurdy, et al., Investigation of Phenolic Bioisosterism in Opiates: 3-Sulfonamido Analogues of Naltrexone and Oxymorphone, Organic Letters. vol. 2, No. 6, pp. 819-821 (2002).
Kubota et al. "Palladium-Catalyzed Cyanation of Hindered, Electron-Rich . . . ", Tetrahedron Ltrs. 8, pp. 799-804 (1998).
Kubota, et al., "Synthesis and Biological Activity of 3-Substituted . . . ", Bioorg. Med. Chem. Ltrs. 8, 799-804 (1998).
Wentland et al., "8-Aminocyclazocine Analogues: Synthesis and Structure . . . ", Bioorg. Med. Chem. Ltrs. 10, pp. 183-187 (2000).
Wentland et al., "Selective Protection and Functionalization of Morphine . . . ", J. Med. Chem. 43, pp. 3558-3565 (2000).
Danso-Danquah, et al., "Synthesis and σ Binding Properties of 2' Substituted", J. Med. Chem. 38, 2978-2985 (1995).
Diaz, et al., SAR & Biological Evaluation of Novel trans-3,4-dimethyl-4-arylpiperidine derivatives as . . . Bioorganic & Medicinal Chemistry Letters 15, pp. 3844-3848 (2005).
Ida, Hisashi "The Nonnarcotic Antitussive Drug Dimemorfan: A Review", Clinical Therapeutics, vol. 19, No. 2, 1997.
Morera et al., "A Palladium-Catalyzed Carbonylative Route to Primary Amides", Tetrahedron Ltrs. 39, pp. 2835-2838 (1998).
Jendralla, et al., "Efficient Kg-Scale Synthesis of Thrombin Inhibitor CRC 220", Tetrahedron vol. 51, No. 44, pp. 12047-12068 (1995).
Cacchi, et al., "Palladium-Catalyzed Carbonylation of Aryl Triflates", Tetrahedron Ltrs. 27, pp. 3931-3934 (1986).
Varma, et al., "Microwave-Accelerated Solvent-Free Synthesis of Thioketones, Thiolactones, Thioamides, Thionoesters, and Thioflavonoids", Organic Letters, vol. 1, No. 5, pp. 697-700 (1999).
Dorwald, F. Zaragoza "Side Reactions in Organic Synthesis", Wiley-VCH, Weinheim p. IX of Preface (2005).
International Preliminary Examination Report for PCT/US01/45581, completed Feb. 5, 2003.
International Search Report for PCT/US01/45581, mailed Aug. 5, 2002.
Mohasci et al., "Acylmorphinans. A Novel Class of Potent Analgesic Agents", Journal of Medicinal Chemistry, 1985, 28(9) 1177-80.
McCurdy et al. Investigation of phenolic bioisosterism in opiates: 3-sulfonamido analogues of naltrexone and oxymorphone. Organic Letters, 2000, 2(6) 819-821.
Zhang et al., "10-Ketomorphinan and 3-Substituted 3-desoxymorphinan Analogues as Mixed k and u Opioid Ligands: Synthesis and Biological Evaluation of Their Binding Affinity at Opioid Receptors," J. Med. Chem. 2004, 47, 165-174.

METHODS OF USING 8-CARBOXAMIDO-2,6-METHANO-3-BENZAZOCINES

CROSS REFERENCE TO RELATED APPLICATIONS

This application is a divisional of copending U.S. application Ser. No. 13/103,599, filed May 9, 2011, now allowed, which was a continuation of U.S. application Ser. No. 12/249,238, filed Oct. 10, 2008, now U.S. Pat. No. 7,956,187, which was a divisional of U.S. application Ser. No. 11/205,354, filed Aug. 17, 2005, now abandoned, which was a divisional of U.S. application Ser. No. 10/987,527, filed Nov. 12, 2004, now U.S. Pat. No. 7,265,226, which was a divisional of U.S. application Ser. No. 10/409,803, filed Apr. 9, 2003, now U.S. Pat. No. 6,887,998, which was a divisional of Ser. No. 10/305,287, filed Nov. 26, 2002, now U.S. Pat. No. 6,784,187. U.S. Ser. No. 10/305,287 was a continuation-in-part of PCT International Application PCT/US01/045581, filed Oct. 31, 2001, and published under PCT Article 21(2) in English as WO 02/36573 on May 10, 2002. PCT/US01/045581 claimed benefit from U.S. Provisional Application 60/244,438, filed Oct. 31, 2000. The entire contents of each of the prior applications are incorporated herein by reference.

STATEMENT AS TO RIGHTS UNDER FEDERALLY-SPONSORED RESEARCH

This invention was made with Government support under Contract No. R01 DA12180, awarded by the National Institutes of Health. Accordingly, the U.S. Government has certain rights in this invention.

FIELD OF THE INVENTION

The invention relates to opioid receptor binding compounds containing carboxamides, formamides, thiocarboxamides and hydroxyamidines. The compounds are useful as analgesics, anesthetics, anti-diarrheal agents, anti-retroviral agents, anticonvulsants, antitussives, anti-cocaine, and anti-addiction medications.

BACKGROUND OF THE INVENTION

Opiates have been the subject of intense research since the isolation of morphine in 1805, and thousands of compounds having opiate or opiate-like activity have been identified. Many opioid receptor-interactive compounds including those used for producing analgesia (e.g., morphine) and those used for treating drug addiction (e.g., naltrexone and cyclazocine) in humans have limited utility due to poor oral bioavailability and a very rapid clearance rate from the body. This has been shown in many instances to be due to the presence of the 8-hydroxyl group (OH) of 2,6-methano-3-benzazocines, also known as benzomorphans [(e.g., cyclazocine and EKC (ethylketocyclazocine)] and the corresponding 3-OH group in morphinanes (e.g., morphine).

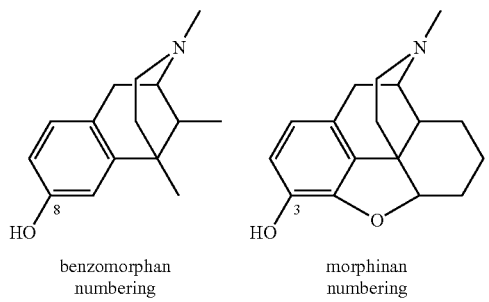 [SMILES: CC1C2Cc3ccc(O)cc3C1(C)CCN2C ; CN1CCC23c4c5ccc(O)c4OC2CCCC3C1C5]

benzomorphan numbering morphinan numbering

The high polarity of these hydroxyl groups retards oral absorption of the parent molecules. Furthermore, the 8-(or 3-)OH group is prone to sulfonation and glucuronidation (Phase II metabolism), both of which facilitate rapid excretion of the active compounds, leading to disadvantageously short half-lives for the active compounds. Unfortunately, the uniform experience in the art of the past seventy years has been that removal or replacement of the 8-(or 3-)OH group has lead to pharmacologically inactive compounds.

SUMMARY OF THE INVENTION

We have now found that the 8-(or 3-)hydroxyl group may be replaced by a number of small, polar, neutral residues, such as carboxamide, thiocarboxamide, hydroxyamidine and formamide groups. Not only do the benzomorphan, morphinan carboxamides have unexpectedly high affinity for opioid receptors, compounds containing these groups in place of OH are far less susceptible to Phase II metabolism and are generally more orally bioavailable. The compounds of the invention are therefore useful as analgesics, anesthetics, anti-pruritics, anti-diarrheal agents, anticonvulsants, antitussives, anorexics and as treatments for hyperalgesia, drug addiction, respiratory depression, dyskinesia, pain (including neuropathic pain), irritable bowel syndrome and gastrointestinal motility disorders. Drug addiction, as used herein, includes alcohol and nicotine addiction. There is evidence in the literature that the compounds may also be useful as anti-retroviral agents, immunosuppressants and antiinflammatories and for reducing ischemic damage (and cardioprotection), for improving learning and memory, and for treating urinary incontinence.

In one aspect, the invention relates to 2,6-methano-3-benzazocine-8-carboxamides and 2,6-methano-3-benzazocine-8-carboxylate esters of formula:

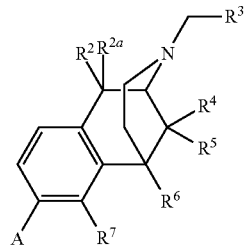

wherein
A is chosen from —CH$_2$—Z, —CN, —NHSO$_2$-(loweralkyl),

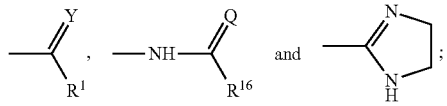

Q is chosen from O, S and NR$^{17}$;
Y is chosen from O, S, NR$^{17}$ and NOH;
Z is chosen from OH, SH, CN and NH$_2$;
R$^1$ is chosen from hydrogen, lower alkoxy, phenyl and —NHR$^8$;
R$^2$ and R$^{2a}$ are both hydrogen or taken together R$^2$ and R$^{2a}$ are =O;
R$^3$ is chosen from hydrogen, lower alkyl, alkenyl, aryl, heterocyclyl, benzyl and hydroxyalkyl;
R$^4$ is chosen from hydrogen, hydroxy, amino, lower alkoxy, C$_1$-C$_{20}$ alkyl and C$_1$-C$_{20}$ alkyl substituted with hydroxy or carbonyl;
R$^5$ is lower alkyl;
R$^6$ is lower alkyl;
R$^7$ is chosen from hydrogen and hydroxy; or
together R$^4$, R$^5$, R$^6$ and R$^7$ may form from one to three rings, said rings having optional additional substitution;
R$^8$ is chosen from hydrogen, —OH, —NH$_2$ and —CH$_2$R$^{15}$;
R$^{15}$ is chosen from hydrogen, alkyl, aryl, substituted aryl and alkyl substituted with alkoxy, amino, alkylamino or dialkylamino;
R$^{16}$ is chosen from hydrogen and NH$_2$; and
R$^{17}$ is chosen from hydrogen, alkyl, aryl and benzyl;
with the provisos that, (1) when R$^2$ and R$^{2a}$ are hydrogen, R$^3$ is hydrogen or cyclopropyl, R$^4$ is hydroxy, and together R$^5$, R$^6$ and R$^7$ form two rings substituted with a spirodioxolane, A cannot be —COOCH$_3$ or NHSO$_2$CH$_3$, (2) when R$^2$ and R$^{2a}$ are hydrogen, R$^3$ is hydrogen or cyclopropyl, R$^4$ is hydroxy, and together R$^5$, R$^6$ and R$^7$ form the ring system of oxymorphone and naltrexone, A cannot be NHSO$_2$CH$_3$; (3) when R$^2$, R$^{2a}$, R$^4$ and R$^7$ are hydrogen, R$^3$ is cyclopropyl and R$^5$ and R$^6$ are methyl, A cannot be —NHC(O)H. The explicit provisos exclude oxymorphone and naltrexone-3-sulfonamides, which were disclosed as having no activity in vitro or in vivo [McCurdy et al. Org. Lett. 2, 819-821 (2000)]; and cyclazocine formamide, which was disclosed as an intermediate in a synthesis in U.S. Pat. Nos. 3,957,793; 4,032,529 and 4,205,171. Additionally, when A is —CN, R$^7$ must be hydroxyl. When R$^4$, R$^5$, R$^6$, and R$^7$ form one to three rings, it is preferred that none of the rings formed by R$^4$, R$^5$, R$^6$, and R$^7$ is aryl or heteroaryl.
Subclasses of the foregoing structure include:
II. 2,6-methano-3-benzazocines of the structure shown above, in which R$^4$, R$^5$, R$^6$ and R$^7$ do not form additional rings;
III. morphinans in which R$^5$ and R$^6$ form one ring:

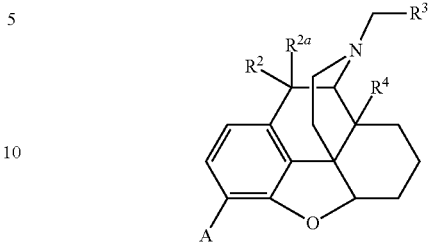

IV. morphinans in which R$^5$, R$^6$ and R$^7$ form two rings:

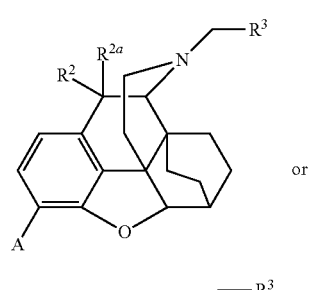

and
V. morphinans wherein R$^4$ and R$^{11}$ form an additional sixth ring, which may be saturated or unsaturated (but not fully aromatic):

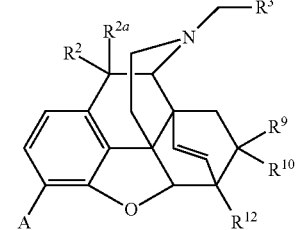

or

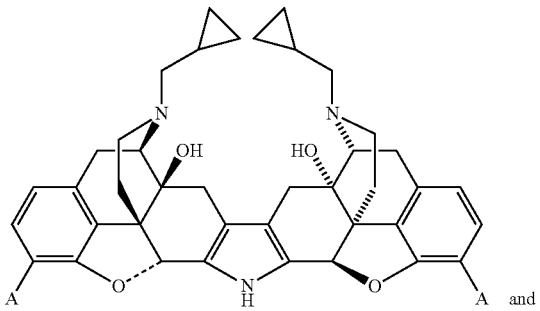

In addition to the major subclasses, there are compounds such as

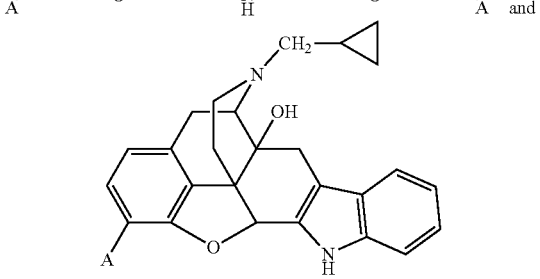

and

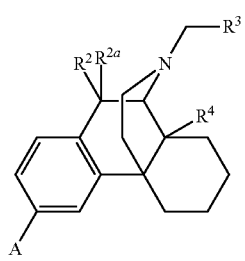

which the person of skill recognizes as closely related to the major subclasses, but which defy easy description in a common Markush structure.

In another aspect, the invention relates to a method for preparing a second compound that interacts with an opioid receptor when a first compound that interacts with an opioid receptor is known. When the first compound contains a phenolic hydroxyl, the method comprises converting the phenolic hydroxyl to a residue chosen from the group described as the variable A above.

In another aspect, the invention relates to a method for decreasing the rate of metabolism of a compound that interacts at an opioid receptor. When the first compound contains a phenolic hydroxyl, the method comprises converting the phenolic hydroxyl to a residue chosen from the group described as the variable A above.

In another aspect, the invention relates to methods for inhibiting, eliciting or enhancing responses mediated by an opioid receptor comprising:
(a) providing a first compound that inhibits, elicits or enhances an opioid receptor response;
(b) preparing a second compound that interacts with an opioid receptor by converting a phenolic hydroxyl group on the first compound to a residue described as A above; and
(c) bringing the second compound into contact with the opioid receptor.

In another aspect, the invention relates to a method for treating a disease by altering a response mediated by an opioid receptor. The method comprises bringing into contact with the opioid receptor a compound having the formula

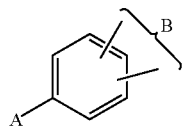

wherein B represents the appropriate residue of a known compound of formula

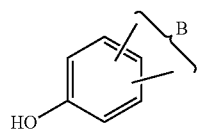

and the known compound of that formula alters a response mediated by an opioid receptor.

In another aspect, the invention relates to processes for converting opioid-binding phenols or phenols on a benzomorphan or morphinan to a carboxamide. The carboxamide conversion processes comprise either:
(a) reacting the phenol with a reagent to convert it to a group displaceable by $CN^\ominus$;
(b) reacting that group with $Zn(CN)_2$ in the presence of a Pd(0) catalyst to provide a nitrile; and
(c) hydrolyzing the nitrile to a carboxamide; or:
(a) reacting the phenol with a reagent to convert the phenol to a triflate;
(b) reacting the triflate with carbon monoxide and ammonia in the presence of a Pd(II) salt and a Pd(0) catalyst to provide a carboxamide; or
(a) reacting the phenol with a reagent to convert the phenol to a triflate;
(b) reacting the triflate with carbon monoxide and hexamethyldisilazane in the presence of a Pd(II) salt and a Pd(0) catalyst to provide a silylated carboxamide precursor; and
(c) hydrolyzing the silylated carboxamide precursor to provide a carboxamide.

Similar processes convert phenols to amidines and thioamides by reacting the foregoing nitrile with hydroxylamine to produce a hydroxyamidine or reacting the foregoing carboxamide with a pentavalent phosphorus-sulfur reagent to produce a thioamide. For the purpose of the invention an "opioid-binding phenol" is one that exhibits binding at an opioid receptor below 25 nM.

DETAILED DESCRIPTION OF THE INVENTION

From many years of SAR studies, it is known that the hydroxyl of morphinans and benzomorphans interacts with a specific site in the opiate receptor. Previous exploration of the tolerance of this site for functional groups other than phenolic hydroxyls has almost uniformly resulted in the complete or near-complete loss of opioid binding. We have now surprisingly found that the hydroxyl can be replaced with one of several bioisosteres. Although a fairly wide range of primary and secondary carboxamides, as well as carboxylates, aminomethyl, hydroxymethyl and even dihydroimidazolyl exhibit binding in the desired range below 25 nanomolar, optimal activity is observed with a carboxamido, thiocarboxamido, hydroxyamidino or formamido group.

Since the hydroxyl functionality of benzomorphans and morphinans can be chemically converted to an amide by a simple, flexible and convenient route described below, and since thiocarboxamido, hydroxyamidino and formamido compounds are also easily synthesized as described below, the door is opened to improving the bioavailability of virtually any of the known and new therapeutic agents that rely on opioid binding for their activity. Moreover, since the receptor seems to tolerate some variation beyond the α-carbon of A, one may contemplate further modulating receptor specificity, affinity and tissue distribution by varying the properties of the alkyl or aryl substituents on A. Preferred residues A are —COOCH$_3$, —COOEt, —CONH$_2$, —C(=S)NH$_2$, —C(O)NHOH, —C(O)NHNH$_2$, —CONHCH$_3$, —CONHBn, —CONHCH$_2$(4-MeOC$_6$H$_4$), 2-(4,5-dihydroimidazolyl), —C(=NOH)NH$_2$, —CH$_2$NH$_2$, CH$_2$OH, —COC$_6$H$_5$, —C(=NOH)C$_6$H$_5$, —NHCHO, —NHCHS and —NHSO$_2$CH$_3$. When $R^7$ is hydroxyl, A may also be —CN. Most preferred are —CONH$_2$, —C(=S)NH$_2$, —C(=NOH)NH$_2$, and —NHCHO.

It is known in the art that compounds that are μ, δ and κ agonists exhibit analgesic activity; compounds that are selective μ agonists exhibit anti-diarrheal activity and are useful in treating dyskinesia; μ antagonists and κ agonists are useful in treating heroin, cocaine, alcohol and nicotine addiction; κ agonists are also anti-pruritic agents and are useful in treating hyperalgesia. Recently it has been found [Peterson et al. *Biochem. Pharmacol.* 61, 1141-1151 (2001)] that κ agonists are also useful in treating retroviral infections. In general, the dextrorotatory isomers of morphinans of type III above are useful as antitussives and anticonvulsants. Additional diseases and conditions for which opioid agonists and antagonists are known to be useful include irritable bowel syndrome, gastrointestinal motility disorder, obesity and respiratory depression. Certain opioids (e.g. fentanyl and derivatives) are useful as anesthetics, i.e., they alter the state of consciousness.

Opioid receptor ligands having known high affinity are shown in the following charts 1 and 2. Replacement of OH in these compounds produces compounds that exhibit similar activity and better bioavailability.

Chart 1. Opioid Receptor Ligands
Benzomorphinans (a.k.a. 2,6-Methano-3-benzazocines)

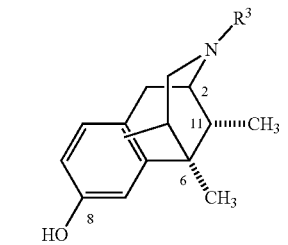

Cyclazocine, $R_3 = CH_2$—c-$C_3H_5$
Metazocine, $R_3 = CH_3$
Phenazocine, $R_3 = CH_2C_6H_5$
SKF 10,047, $R_3 = CH_2CH=CH_2$
Pentazocine, $R_3 = CH_2CH=C(CH_3)_2$
(all racemic)

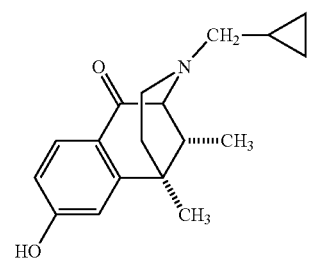

Ketocyclazocine

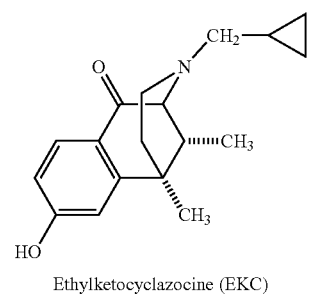

Ethylketocyclazocine (EKC)

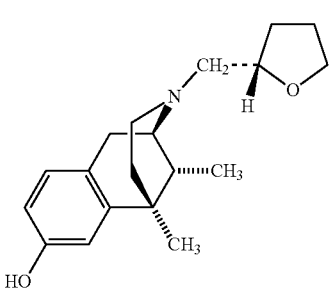

MR2034-"Merz" core
structure (opt. active)

-continued

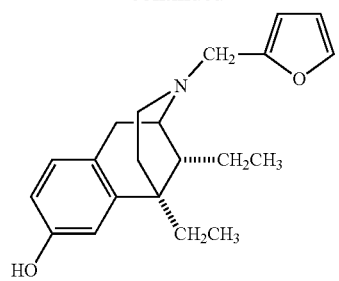

MR2266

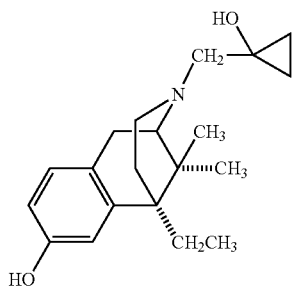

Bremazocine

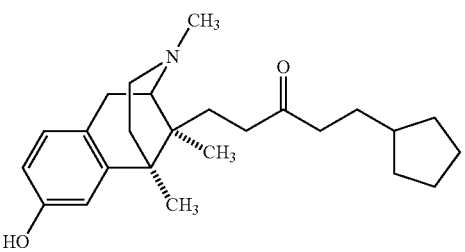

WIN 44,441

Chart 2. Opioid Receptor Ligands Morphine and Morphinans

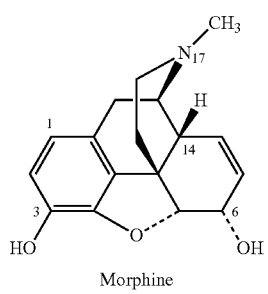

Morphine

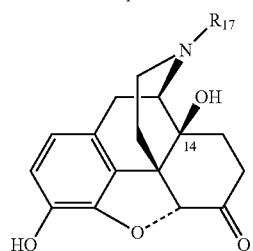

Naltrexone; $R_{17} = CH_2$-c-$C_3H_5$
Naloxone; $R_{17} = CH_2CH=CH_2$
Nalmexone; $R_{17} = CH_2CH=C(CH_3)_2$
Oxymorphone; $R_{17} = CH_3$

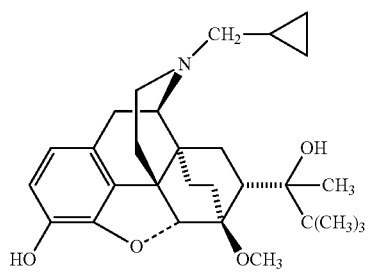
Buprenorphine
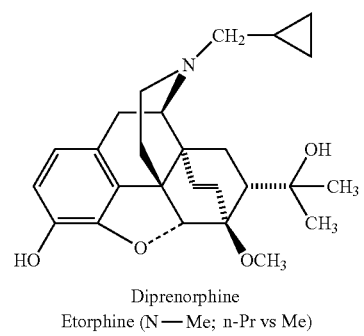
Diprenorphine
Etorphine (N—Me; n-Pr vs Me)
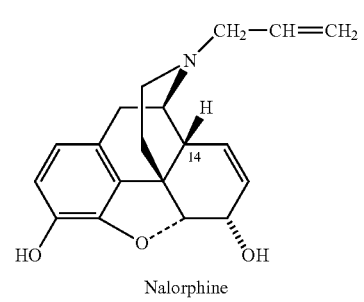
Nalorphine
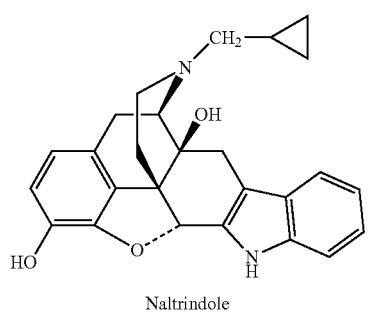
Naltrindole
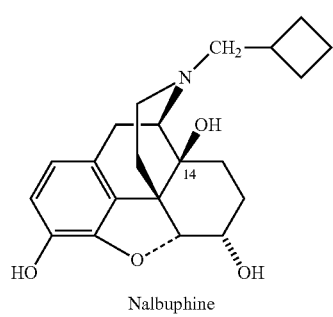
Nalbuphine
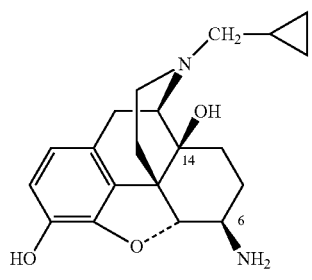
β-Naltrexamine
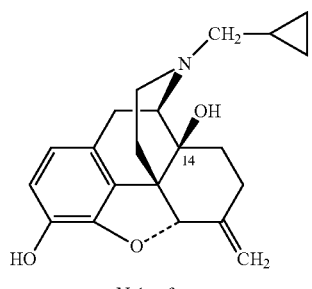
Nalmefene
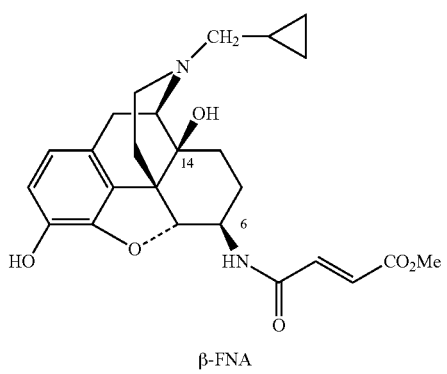
β-FNA
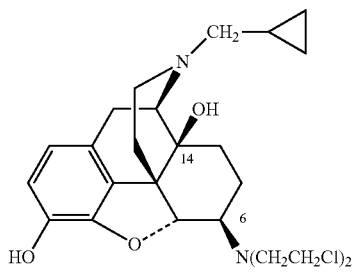
β-CNA
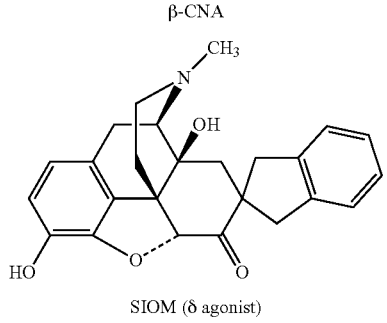
SIOM (δ agonist)

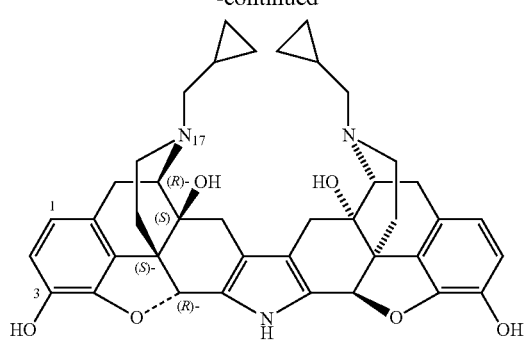

nor-BNI (Norbinaltorphimine)
Reg # = 105618-26-6

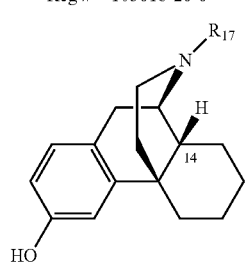

Levorphanol; $R_{17}$ = $CH_3$
Cyclorphan; $R_{17}$ = $CH_2$-c-$C_3H_5$
MCL 101; $R_{17}$ = $CH_2$-c-$C_4H_7$
Butorphanol; $R_{17}$ = $CH_2$-c-$C_4H_7$
and 14-OH
Merz-morphinane hybrid core; $R_{17}$ = $CH_2$——(S)-tetrahydrofurfuryl

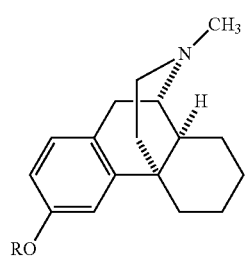

Dextromethorphan; R = $CH_3$
Dextrorphan; R = H
(note "opposite" sterochemistry)

Chart 3-Miscellaneous Opioid Receptor Ligands

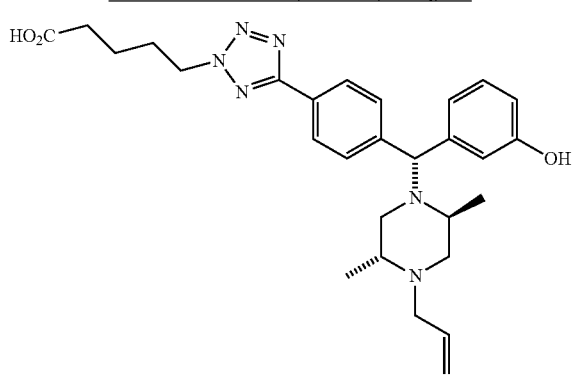

Registry Number 216531-48-5

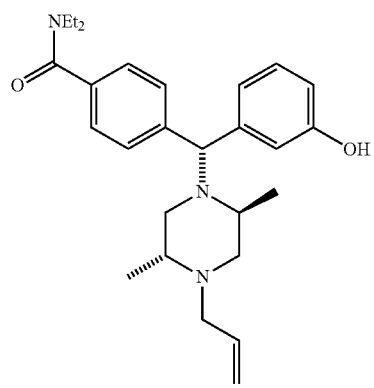

Registry Number 155836-52-5

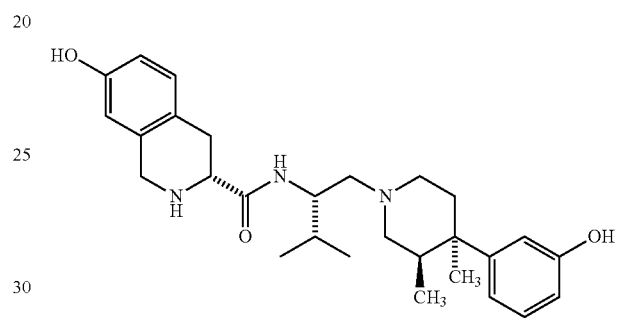

Registry number 361444-66-8

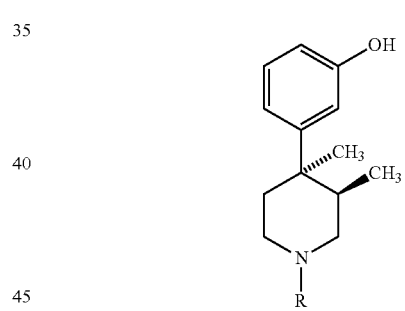

R = $CH_3$; Registry Number: 69926-34-7
R = $CH_2CH_2CH(OH)C_6H_{11}$; Registry Number: 119193-09-8
R = $CH_2CH(CH_2Ph)CONHCH_2CO_2H$; Registry Number: 156130-44-8
R = $(CH_2)_3CH(CH_3)_2$; Registry Number: 151022-07-0
R = $(CH_2)_3$-2-thienyl; Registry Number: 149710-80-5

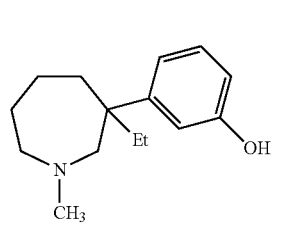

Meptazinol
Registry Number 59263-76-2

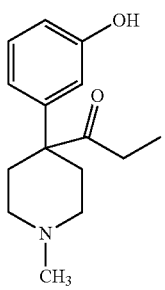

Ketobemidone
Registry Number 469-79-4

-continued

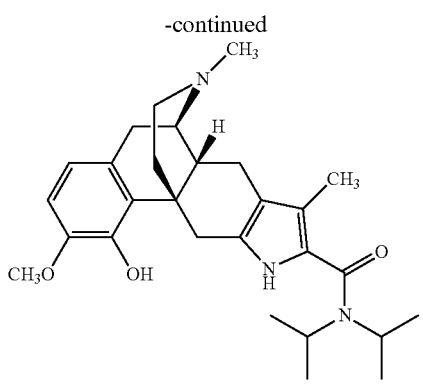

Registry number 177284-71-8

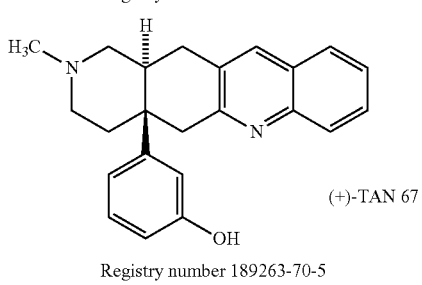

(+)-TAN 67

Registry number 189263-70-5

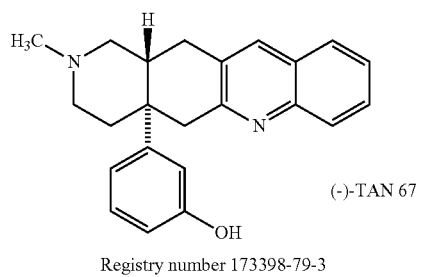

(-)-TAN 67

Registry number 173398-79-3

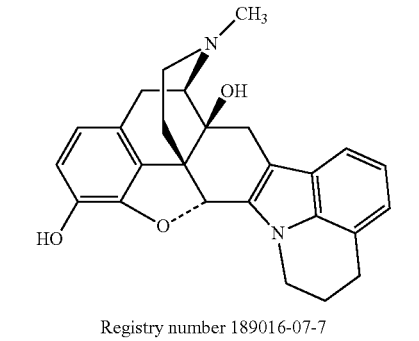

Registry number 189016-07-7

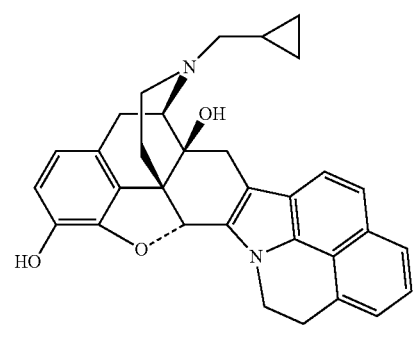

Registry number 189015-08-5

Other opioid receptor ligands are described in Aldrich, J. V. "Analgesics" in *Burger's Medicinal Chemistry and Drug Discovery*, M. E. Wolff ed., John Wiley & Sons 1996, pages 321-44, the disclosures of which are incorporated herein by reference.

We have examined the opioid receptor binding of a series of analogs of known compounds that interact at opioid receptors in which the OH is replaced by the R-group shown in Tables 1-4. The standards are shown in Table 5. The affinities of the compounds of the invention were determined in guinea pig brain cells by the method described in Wentland et al. *Biorgan. Med. Chem. Lett.* 9. 183-187 (2000). Alternatively, where noted, the affinities of the compounds of the invention were determined in cloned human receptors in Chinese hamster ovary cells by the method described by Xu et al [*Synapse* 39, 64-69 (2001)]. CHO cell membranes, expressing the human μ, δ, or κ opioid receptor, were incubated with 12 different concentrations of the compounds in the presence of receptor-specific radioligands at 25° C., in a final volume of 1 ml of 50 mM Tris-HCl, pH 7.5. Nonspecific binding was determined using 1 μM naloxone. Data are the mean value±S.E.M. from three experiments, performed in triplicate.

TABLE 1

Cyclazocine subseries $K_i$ (nM ± S.E.)

| example | A = | [$^3$H] DAMGO (μ) | [$^3$H] Naltrindole (δ) | [$^3$H] U69,593 (κ) |
|---|---|---|---|---|
| 1 | CN | 540 ± 50 | 2700 ± 1400 | 71 ± 13 |
| 2 | COOH | 58 ± 1.8 | 320 ± 14 | 31 ± 0.87 |
| 3 | CO$_2$CH$_3$ | 45 ± 0.92 | 59 ± 2.1 | 2.0 ± 0.21 |
| 4 | CONH$_2$ | 0.41 ± 0.07 | 8.3 ± 0.49 | 0.53 ± 0.06 |
| 4 | CONH$_2$ | 0.32 ± 0.04 | NT | 0.60 ± 0.04 |
| 4 | CONH$_2$ · HCl | 0.34 ± 0.01 | 4.9 ± 0.80 | 0.42 ± 0.02 |
| 4a | (−)CONH$_2$ | 0.17 ± 0.04 | 2.6 ± 0.6 | 0.28 ± 0.01 |
| 4b | (+)CONH$_2$ | 63 ± 5.4 | 570 ± 50 | 67 ± 1.6 |
| 5 | C(=S)NH$_2$ | 0.22 ± 0.02 | 4.0 ± 0.48 | 0.67 ± 0.01 |
| 6 | CONHOH | 12 ± 0.32 | 210 ± 40 | 6.9 ± 0.61 |
| 7 | CONHNH$_2$ | 60 ± 9.3 | 450 ± ∀ 62 | 19 ± 1.4 |
| 8 | CONHCH$_3$ | 24 ± 1.6 | 63 ± 4.1 | 2.6 ± 0.19 |
| 9 | CONHCH$_2$C$_6$H$_5$ | 20 ± 2.2 | 140 ± 18 | 78 ± 7.6 |
| 10 | CONHCH$_2$(4-MeOC$_6$H$_4$) | 19 ± 1.5 | 150 ± 17 | 110 ± 3.1 |
| 11 | CONHCH$_2$CH$_2$N(CH$_3$)$_2$ | 26 ± 2.9 | 350 ± 51 | 44 ± 11 |
| 12 | CONH(CH$_2$)$_3$N(CH$_3$)$_2$ | 370 ± 54 | 3000 ± 230 | 310 ± 64 |
| 13 | 2-(4,5-H$_2$)-imidazolyl | 23 ± 1.9 | 55 ± 5.1 | 11 ± 0.69 |
| 14 | C(=NOH)NH$_2$ | 3.8 ± 0.42 | 16 ± 0.67 | 0.90 ± 0.15 |
| 15 | CH$_2$NH$_2$ | 31 ± 5.4 | 390 ± 47 | 17 ± 2.9 |
| 16 | CH$_2$OH | 21 ± 2.0 | 210 ± 29 | 7.6 ± 0.80 |
| 17 | COC$_6$H$_5$ | 33 ± 0.90 | 490 ± 43 | 19 ± 2.6 |
| 18 | C(=NOH)C$_6$H$_5$ | 86 ± 3.8 | 180 ± 15 | 7.2 ± 0.40 |
| 38 | CH$_2$CN | 3.3 ± 1.5 [a] | 2000 ± 685 [a] | 2.9 ± 0.36 [a] |
| 39 | CH(N=OH) | 18 ± | 140 ± | 0.73 ± |

TABLE 1-continued

Cyclazocine subseries

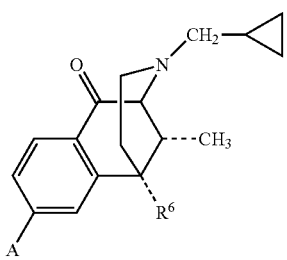

$K_i$ (nM ± S.E.)

| example | A = | [³H] DAMGO (μ) | [³H] Naltrindole (δ) | [³H] U69,593 (κ) |
|---|---|---|---|---|
| | | 1.8 [a] | 15 [a] | 0.03 [a] |
| 19 | NHCHO | 1.9 ± 0.14 | 37 ± 3.9 | 0.85 ± 0.080 |
| 19a | (−)NHCHO | 1.1 ± 0.04 | 9.8 ± 0.28 | 0.49 ± 0.012 |
| 19b | (+)NHCHO | 2300 ± 180 | >10,000 | 900 ± 8.7 |
| 20 | NHCHS | 0.76 ± 0.09 | 16 ± 0.30 | 0.63 ± 0.15 |
| 21 | NHSO$_2$CH$_3$ | 15 ± 1.2 | 780 ± 170 | 21 ± 1.5 |
| 36 | NHCONH$_2$ | 20 ± 0.66 | 90 ± 12 | 15 ± 1.4 |
| 37 | NHCSNH$_2$ | 10 ± 1.7 [a] | 440 ± 72 [a] | 4.0 ± 0.54 [a] |

[a] data from chinese hamster ovary rather than guinea pig brain

TABLE 2

Keto subseries:

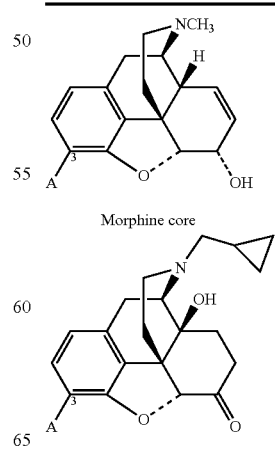

$R^6$ = CH$_3$ (ketocyclazocine)
$R^6$ = CH$_2$CH$_3$ (EKC)

| example | A = | [³H] DAMGO (μ) | [³H] Naltrindole (δ) | [³H] U69,593 (κ) |
|---|---|---|---|---|
| 22 | CN (KC) | 680 ± 61 | 3400 ± 410 | 59 ± 0.77 |
| 23 | CONH$_2$ (KC) | 1.4 ± 0.07 | 20 ± 2.3 | 1.8 ± 0.10 |
| 24 | CONH$_2$ (EKC) | 1.2 ± 0.12 | 9.8 ± 0.50 | 0.70 ± 0.08 |
| 40 | NHCHO (EKC) | 6.1 ± 0.83 | 52 ± 3.4 | 1.2 ± 0.11 |

TABLE 3

Merz subseries

| example | A = | [³H] DAMGO (μ) | [³H] Naltrindole (δ) | [³H] U69,593 (κ) |
|---|---|---|---|---|
| 25 | (−)-(2″ S)-8-OH | 0.19 ± 0.01 | 3.6 ± 0.40 | 0.09 ± 0.01 |
| 26 | (−)-(2″ S)-8-CONH$_2$ | 0.052 ± 0.013 | 2.0 ± 0.15 | 0.089 ± 0.004 |
| 27 | (−)-(2″ R)-8-OH | 4.0 ± 0.54 | 67 ± 4.3 | 1.5 ± 0.07 |
| 28 | (−)-(2″ R)-8-CONH$_2$ | 2.9 ± 0.17 | 34 ± 0.10 | 2.8 ± 0.24 |
| 29 | (−)-(2″ S)-8-CH$_2$NH$_2$ | 28 ± 2.3 | 300 ± 27 | 18 ± 1.9 |

TABLE 4

Other Series

| example | A = | [³H] DAMGO (μ) | [³H] Naltrindole (δ) | [³H] U69,593 (κ) |
|---|---|---|---|---|
| 30 | CONH$_2$ (morphine) | 34 ± 1.8 | 1900 ± 81 | 2000 ± 97 |
| 31 | CONHCH$_3$ (morphine) | 440 ± 9.2 | >10,000 | >10,000 |
| 32 | CONH$_2$ (naltrexone) | 1.9 ± 0.21 | 110 ± 8.1 | 22 ± 0.85 |
| 33 | CO$_2$Et (naltrexone) | 24 ± 1.7 | 970 ± 155 | 16 ± 0.70 |
| 41 | (−) NHCHO (naltrexone) | 4.1 ± 0.40 [a] | 280 ± 7.6 [a] | 2.3 ± 0.044 [a] |
| 34 | CONH$_2$ (naltrindole) | 47 ± 2.7 | 0.33 ± 0.04 | 99 ± 7.9 |
| 35 | CONH$_2$ (buprenorphine) | 2.3 ± 0.29 | 7.3 ± 0.61 | 4.3 ± 0.05 |
| 42 | CONH$_2$ (nalbuphine) | 3.8 ± 0.62 [a] | 150 ± 82 [a] | 0.46 ± 0.04 [a] |
| 43 | CN (7-OH) | 0.35 ± 0.092 [a] | 82 ± 24 [a] | 2.6 ± 0.21 [a] |
| 44 | CONH$_2$ (butorphanol) | 0.15 ± 0.019 [a] | 14 ± 2.1 [a] | 0.39 ± 0.057 [a] |

Morphine core

Naltrexone core

TABLE 4-continued

Other Series

| example | A = | [³H]DAMGO (μ) | [³H]Naltrindole (δ) | [³H]U69,593 (κ) |
|---|---|---|---|---|

Naltrindole core

Buprenorphine core

Nalbuphine core

Butorphanol core 43 (a 7-hydroxybenzomorphan)

TABLE 5

Standards

| | [³H]DAMGO (μ) | [³H]Naltrindole (δ) | [³H]U69,593 (κ) |
|---|---|---|---|
| (±)-Cyclazocine | 0.32 ± 0.02 | 1.1 ± 0.04 | 0.18 ± 0.020 |
| (±)-Cyclazocine | 0.16 ± 0.01$^a$ | 2.0 ± 0.22$^a$ | 0.07 ± 0.01$^a$ |
| (+)-Cyclazocine | 360 ± 16 | 1100 ± 63 | 76 ± 8.2 |
| (−)-Cyclazocine | 0.10 ± 0.03 | 0.58 ± 0.06 | 0.052 ± 0.009 |
| (±)-EKC | 0.78 ± 0.10 | 3.4 ± 0.41 | 0.62 ± 0.11 |
| (±)-ketocyclazocine | 3.3 ± 0.66 | 20 ± 2.7 | 1.0 ± 0.24 |
| (±)-ketocyclazocine | 1.7 ± 0.21$^a$ | 130 ± 14$^a$ | 1.0 ± 0.019$^a$ |
| naltrexone (3-OH) | 0.17 ± 0.03 | 11 ± 1.1 | 0.31 ± 0.03 |
| naltrindole (3-OH) | 13 ± 1.1 | 0.13 ± 0.02 | 4.6 ± 0.23 |
| buprenorphine | 0.98 ± 0.11 | 0.72 ± 0.10 | 0.90 ± 0.11 |
| nalbuphine | 1.6 ± 0.37$^a$ | 580 ± 80$^a$ | 3.0 ± 0.63$^a$ |
| butorphanol | 0.12 ± 0.058$^a$ | 12 ± 3.8$^a$ | 0.22 ± 0.023$^a$ |

Example 4 was tested several times independently to confirm the $K_i$'s. Inspection of the results in Table 1 indicates not only that affinity is preserved in the compounds of the invention, but also that receptor selectivity can be modulated.

Antinociceptive activity is evaluated by the method described in Jiang et al. [*J. Pharmacol. Exp. Ther.* 264, 1021-1027 (1993), page 1022]. Compound 4 was found to exhibit an $ED_{50}$ of 0.21 nmol in the mouse acetic acid writhing test when administered i.c.v. Its "parent" cyclazocine exhibited an $ED_{50}$ of 2.9 nmol i.c.v. The time courses in producing antinociception in the mouse writhing test were compared for compound 4 and cyclazocine. Mice were injected with 1.0 mg/kg of either compound 4 or cyclazocine, given by i.p. administration. An increase in the duration of action from ca. 2 hr to 15 hr was observed for compound 4 compared to cyclazocine.

Definitions

Throughout this specification the terms and substituents retain their definitions.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, cyclopropyl, butyl, s-and t-butyl, cyclobutyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. Heteroaryl refers to any maximally unsaturated heterocycle. The aromatic 6- to 14-membered carbocyclic rings include, e.g., benzene, naphthalene, indane, tetralin, and fluorene and the 5- to 10-membered aromatic heterocyclic rings include, e.g., pyrrole, imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like. Heteroarylalkyl means an alkyl residue attached to a heteroaryl ring. Examples include, e.g., pyridinylmethyl, pyrimidinylethyl and the like.

Heterocycle means a cycloalkyl or aryl residue in which one to two of the carbons is replaced by a heteroatom such as oxygen, nitrogen or sulfur. Heteroaryls form a subset of heterocycles. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like.

Substituted alkyl, aryl, cycloalkyl, or heterocyclyl refer to alkyl, aryl, cycloalkyl, or heterocyclyl wherein up to three H atoms in each residue are replaced with halogen, hydroxy, loweralkoxy, carboxy, carbalkoxy, carboxamido, cyano, carbonyl, —NO$_2$, —NR$^1$R$^2$; alkylthio, sulfoxide, sulfone, acylamino, amidino, phenyl, benzyl, heteroaryl, phenoxy, benzyloxy, heteroaryloxy, or substituted phenyl, benzyl, heteroaryl, phenoxy, benzyloxy, or heteroaryloxy.

Virtually all of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, as well as their racemic and optically pure forms. In general it has been found that the levo isomer of morphinans and benzomorphans is the more potent antinociceptive agent, while the dextro isomer may be useful as an antitussive or antispasmodic agent. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

Abbreviations

The following abbreviations and terms have the indicated meanings throughout:

| | |
|---|---|
| Ac = | acetyl |
| BNB = | 4-bromomethyl-3-nitrobenzoic acid |
| Boc = | t-butyloxy carbonyl |
| Bu = | butyl |
| c- = | cyclo |
| DAMGO = | Tyr-ala-Gly-NMePhe-NHCH$_2$OH |
| DBU = | diazabicyclo[5.4.0]undec-7-ene |
| DCM = | dichloromethane = methylene chloride = CH$_2$Cl$_2$ |
| DEAD = | diethyl azodicarboxylate |
| DIC = | diisopropylcarbodiimide |
| DIEA = | N,N-diisopropylethyl amine |
| DMAP = | 4-N,N-dimethylaminopyridine |
| DMF = | N,N-dimethylformamide |
| DMSO = | dimethyl sulfoxide |
| DPPF = | 1,1'-bis(diphenylphosphino)ferrocene |
| DVB = | 1,4-divinylbenzene |
| EEDQ = | 2-ethoxy-1-ethoxycarbonyl-1,2-dihydroquinoline |
| Fmoc = | 9-fluorenylmethoxycarbonyl |
| GC = | gas chromatography |
| HATU = | O-(7-Azabenzotriazol-1-yl)-1,1,3,3-tetramethyluronium hexafluorophosphate |

-continued

| | |
|---|---|
| HOAc = | acetic acid |
| HOBt = | hydroxybenzotriazole |
| Me = | methyl |
| mesyl = | methanesulfonyl |
| MTBE = | methyl t-butyl ether |
| NMO = | N-methylmorpholine oxide |
| PEG = | polyethylene glycol |
| Ph = | phenyl |
| PhOH = | phenol |
| PfP = | pentafluorophenol |
| PPTS = | pyridinium p-toluenesulfonate |
| PyBroP = | bromo-tris-pyrrolidino-phosphonium hexafluorophosphate |
| rt = | room temperature |
| sat'd = | saturated |
| s- = | secondary |
| t- = | tertiary |
| TBDMS = | t-butyldimethylsilyl |
| TFA = | trifluoroacetic acid |
| THF = | tetrahydrofuran |
| TMOF = | trimethyl orthoformate |
| TMS = | trimethylsilyl |
| tosyl = | p-toluenesulfonyl |
| Trt = | triphenylmethyl |

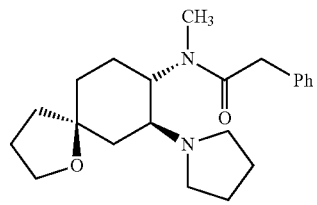

In the general processes described below, the preferred reagent to convert a phenol to a group displaceable by CN$^\ominus$ is trifluoromethansulfonic anhydride, which is usually employed in the presence of base. Other reagents are known to persons of skill in the art to convert phenols to groups that may be displaced by cyanide anion. The advantage of the trifluoromethansulfonic anhydride procedure is that it allows displacement under conditions that are mild enough to avoid destruction of the rest of the molecule for most species of interest. Other reagents are operable, but require more robust substrates than may be of interest in a particular case. The consideration of which to use is within the skill of the artisan. A preferred Pd(0) catalyst for use in the displacement with zinc cyanide is tetrakis(triphenylphosphine)palladium. In the direct displacements with carbon monoxide and ammonia or an ammonia equivalent, the preferred Pd(0) catalyst is generated in situ from Pd(OAc)$_2$ or PdCl$_2$ and 1,1'-bis(diphenylphosphino)ferrocene. Other Pd(0) ligands include DPPF, DPPP, triphenylphosphine, 1,3-bis(diphenylphosphino)propane, BINAP and xantphos. The preferred pentavalent phosphorus-sulfur reagents for converting carboxamides to thiocarboxamides are Lawesson's reagent and phosphorus pentasulfide.

It may happen that residues in the substrate of interest require protection and deprotection during the conversion of the phenol to the desired bioisostere. Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

The compounds of the invention are synthesized by one of the routes described below:

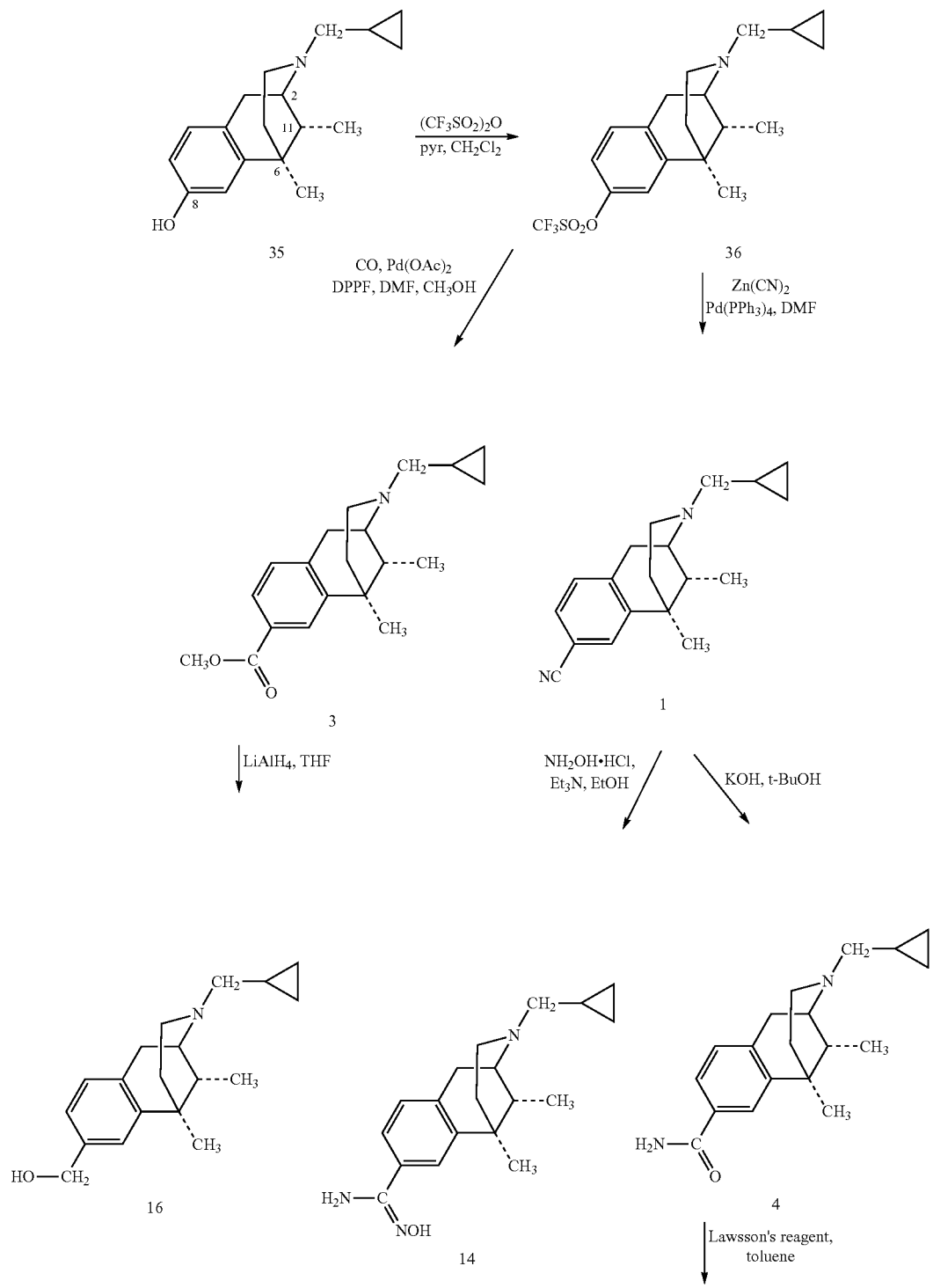

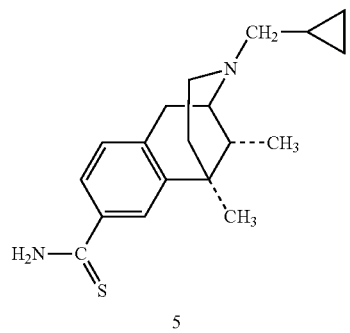

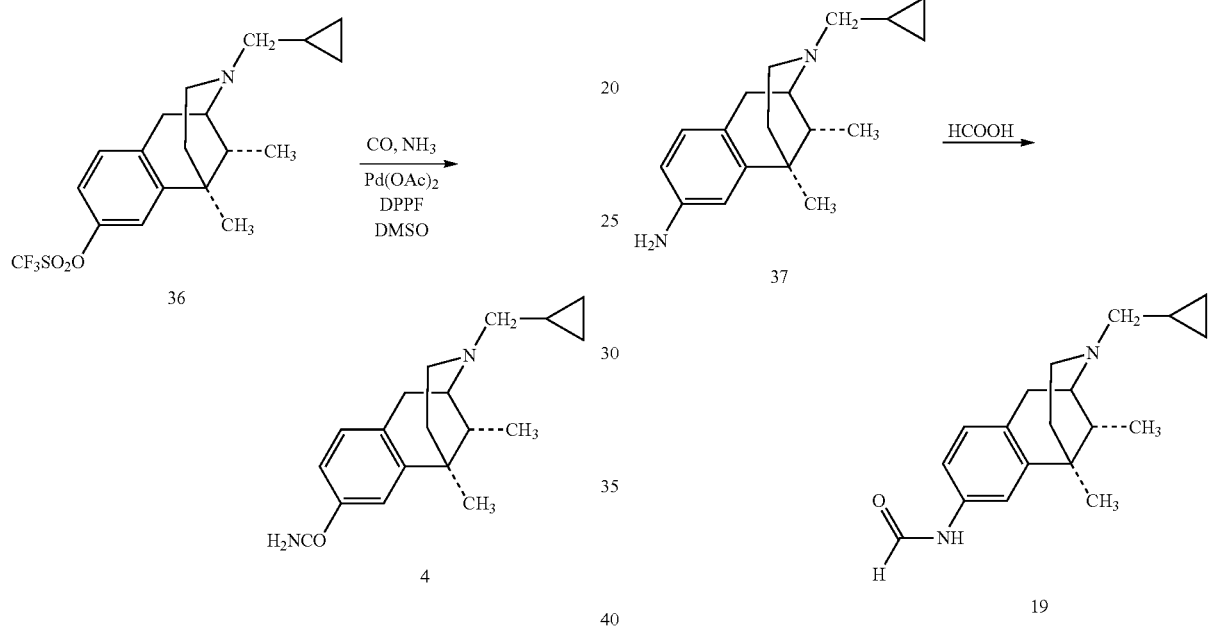

Scheme 2-Alternate Carboxamide Synthesis

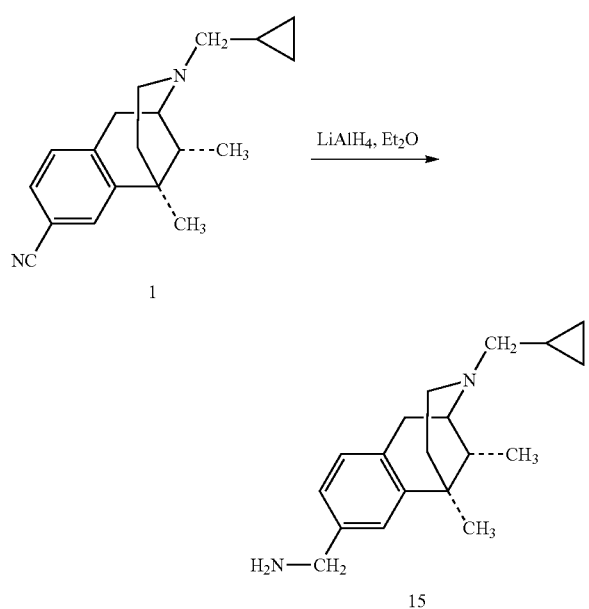

Chemical Syntheses

Proton NMR [Varian Unity-500 (500 MHz) NMR] data, direct insertion probe (DIP) chemical ionization mass spectra (Shimadzu GC-17A GC-MS mass spectrometer), and infrared spectra (Perkin-Elmer Paragon 1000 FT-IR spectrophotometer) were consistent with the assigned structures of all test compounds and intermediates. $^1$H NMR multiplicity data are denoted by s (singlet), d (doublet), t (triplet), q (quartet), m (multiplet), and br (broad). Coupling constants are in hertz. Carbon, hydrogen, and nitrogen elemental analyses for all novel targets were performed by Quantitative Technologies Inc., Whitehouse, N.J., and were within ±0.4% of theoretical values except as noted; the presence of water was conformed by proton NMR. Melting points were determined on a Melt-emp capillary melting point apparatus and are uncorrected. Optical rotation data were obtained from a Perkin-Elmer 241 polarimeter. Reactions were generally performed under a $N_2$ atmosphere. Amines used in the Pd-catalyzed amination reactions and racemic-2,2'-bis(diphenylphosphino)-1,1'-binapthyl (BINAP) were purchased from Aldrich Chemical Company and used as received unless otherwise indicated. Tris(dibenzylideneacetone) dipalladium (0) [$Pd_2(dba)_3$], $Pd(OAc)_2$, 1,1'-bis(diphenylphosphino)ferrocene (DPPF), were purchased from Strem Chemicals, Incorporated. Toluene and Et$_2$O were distilled from sodium metal. THF was distilled from sodium/benzophenone ketyl. Pyridine was distilled from KOH. Methylene chloride was distilled from CaH$_2$. DMF and DMSO were distilled from CaH$_2$ under reduced pressure. Methanol was dried over 3± molecular sieves prior to use. Silica gel (Bodman Industries, ICN SiliTech 2-63 D 60A, 230-400 Mesh) was used for flash column chromatography.

(±)-3-(Cyclopropylmethyl)-1,2,3,4,5,6-hexahydro-cis-6,11-dimethyl-2,6-methano-3-benzazocin-8-carbonitrile [1]. The triflate [36] of cyclazocine [35] (470 mg, 1.166 mmol), obtained by the method of Wentland et al. [*Bioorgan. Med. Chem. Lett.* 9, 183-187 (2000)], was dissolved in 20 mL DMF and Zn(CN)$_2$ (272.6 mg, 2.322 mmol) and Pd(PPh$_3$)$_4$ (53.9 mg, 0.0466 mmol) were added. After heating in 120° C. for 2 h, the reaction was allowed to stir at 25° C. overnight. A mixture of EtOAc and NaHCO$_3$ solution was then added. The organic phase was washed with brine and then dried over anhydrous Na$_2$SO$_4$, filtered and concentrated in vacuo to dryness. Flash column chromatography gave 1 as a colorless oil (260 mg, 80%). $^1$H-NMR (500 MHz, CDCl$_3$) d 7.52 (b,1H), 7.37 (dd, J=7.8, 1.5 Hz, 1H), 7.14 (d, J=8.1, 1H), 3.15 (m, 1H), 2.96 (d, J=19.0 Hz, 1H), 2.66-2.74 (m, 2H), 2.45 (m, 1H), 2.30 (m, 1H), 1.84-1.98 (m, 3H), 1.38 (s, 3H), 1.29 (m, 1H), 0.85 (m, 1H), 0.82 (d, J=7.1 Hz, 3H), 0.51 (m, 2H), 0.10 (m, 2H). IR (film) 2961, 2918, 2225 cm$^{-1}$. CI-MS, m/z (relative intensity) 281 (M+1, 100%). Anal. Calcd. for C$_{19}$H$_{24}$N$_2$.0.125H$_2$O: C 80.78, H 8.59, N 9.92. Found: C 80.75, H 8.63, N 9.89.

(±)-3-(Cyclopropylmethyl)-1,2,3,4,5,6-hexahydro-cis-6,11-dimethyl-2,6-methano-3-benzazocin-8-carboxamide [4]. Compound 1 (80 mg, 0.286 mmol) was dissolved in about 1 mL t-butyl alcohol. KOH (58.8 mg, 1.05 mmol) was then added. The reaction mixture was stirred at reflux for about 20 min and the solvent was evaporated and CH$_2$Cl$_2$ and MeOH and NaCl solution were added. The organic phase was washed with brine and then dried over anhydrous Na$_2$SO$_4$, filtered and concentrated in vacuo to dryness to give 4 as white foam (80 mg, 95%). $^1$H-NMR (500 MHz, CD$_3$OD) d 7.81 (m, 1H), 7.62 (m, 1H), 7.17 (m, 1H), 3.22 (m, 1H), 3.04 (m, 1H), 2.66-2.82 (m, 2H), 2.50 (m, 1H), 2.35 (m, 1H), 1.86-1.98 (m, 3H), 1.34 (s, 3H), 1.36 (m, 1H), 0.88 (m, 1H), 0.84 (d, J=7.0 Hz, 3H), 0.54 (m, 2H), 0.16 (m, 2H). $^{13}$C-NMR (500 MHz, CD$_3$OD) d 172.71, 143.32, 142.34, 133.01, 128.61, 126.61, 126.18, 60.67, 58.09, 46.92, 42.74, 42.38, 37.69, 25.92, 25.07, 14.62, 9.67, 4.64, 4.52. IR (film) 1654.2 cm$^{-1}$. CI-MS, m/z (relative intensity) 299 (M+1, 100%). Anal. Calcd. for C$_{19}$H$_{26}$N$_2$O.0.25H$_2$O: C 75.37, H 8.76, N 9.26. Found: C 75.27, H 9.02, N 9.03.

(±)-3-(Cyclopropylmethyl)-1,2,3,4,5,6-hexahydro-cis-6,11-dimethyl-2,6-methano-3-benzazocin-8-carboxamide [1] (alternate procedure). A flask containing triflate 36 (100 mg), Pd(OAc)$_2$ (10.2 mg), and 1,1'-bis(diphenylphosphino)ferrocene(DPPF, 25 mg) was purged with argon. The argon was replaced with gaseous CO and the reaction vessel was closed to the atmosphere. Dry DMSO (1.25 mL) was added via syringe and gaseous ammonia was added to the resulting mixture via a canula. A balloon was used to keep the additional volume contained. The mixture was stirred for 17 h at 70° C. followed by cooling to 25° C. The reaction mixture was diluted with water and the product was extracted into ethyl acetate. The organic extracts was washed with aqueous NaHCO$_3$ and dried (Na$_2$SO$_4$). Concentration of the solvent in vacuo gave 90 mg of a crude product. This material was purified via flash chromatography (25:1:0.1—CH$_2$Cl$_2$: MeOH:conc NH$_4$OH) to provide 47 mg (65.3%) of compound 4.

(±)-3-(Cyclopropylmethyl)-1,2,3,4,5,6,-hexahydro-cis-6,11-dimethyl-2,6-methano-3-benzazocin-8-carboxylic acid methyl ester [3]. A modification of a known procedure (Cacchi, S.; Ciattini, P. G.; Morera, E.; Ortar, G. *Tetrahedron Lett.* 1986, 27, 3931-3934) was used in this preparation. Under an argon atmosphere, triethylamine (0.30 mL, 2.15 mmol) was added to a mixture of the 8-triflate ester of cyclazocine [36] (0.403 g, 1.0 mmol), palladium acetate (0.0068 g, 0.03 mmol), 1,1'-bis(diphenylphosphino)ferrocene (0.00166 g, 0.03 mmol) and methanol (1 mL, 22.2 mmol) in DMF (1 mL). The solution was purged with carbon monoxide for 15 min and stirred under a CO balloon at 70° C. for 5 h. The reaction mixture was taken up in 20 mL of ethyl acetate and washed with saturated sodium bicarbonate solution and water. The organic phase was dried with sodium sulfate and evaporated to give crude product as a brown oil. Chromatography on silica gel using CH$_2$Cl$_2$:MeOH:NH$_4$OH (conc)/40:1:0.1 provided the desired compound 3 (0.235 g, 86.6%) as a colorless oil: $^1$H NMR (500 MHz, CDCl$_3$) δ 7.93 (d, J=1.7 Hz, 1H), 7.76 (dd, J$_1$=1.7 Hz, J$_2$=7.8 Hz, 1H), 7.12 (d, J=7.8 Hz, 1H), 3.89 (s, 3H), 3.15 (m, 1H), 2.96 (d, J=19.0 Hz, 1H), 2.73 (d, J=6.1 Hz, 1H), 2.70 (m, 1H), 2.46 (dd, J$_1$=7.3 Hz, J$_2$=12.4 Hz, 1H), 2.31 (dd, J$_1$=6.6 Hz, J$_2$=12.4 Hz, 1H), 1.96 (m, 1H), 1.91 (m, 2H), 1.43 (s, 3H), 1.33 (m, 1H), 0.86 (m, 1H), 0.83 (d, J=7.1 Hz, 3H), 0.51 (d, J=8.1 Hz, 2H), 0.11 (m, 2H); IR (film) ν$_{max}$ 2916, 1720, 1270 cm$^{-1}$; MS (CI) m/z 314 (M+H)$^+$; Anal. calc. for C$_{20}$H$_{27}$NO$_2$: C, 76.64; H, 8.68; N, 4.47. Found: C, 76.37; H, 8.93; N, 4.38.

(±)-[3-(Cyclopropylmethyl)-1,2,3,4,5,6,-hexahydro-cis-6,11-dimethyl-2,6-methano-3-benzazocin-8-yl]-methanol [16]. Under a blanket of N$_2$ at 0° C., (±)-3-(cyclopropylmethyl)-1,2,3,4,5,6,-hexahydro-cis-6,11-dimethyl-2,6-methano-3-benzazocin-8-carboxylic acid methyl ester [3] (0.1062 g, 0.34 mmol), LiAlH$_4$ powder (0.0258 g, 0.68 mmol) and dry THF (0.77 mL) were placed in a one-neck round bottom flask equipped with condenser and stir bar. The ice/water bath was removed and the reaction was stirred at reflux for 24 h. The mixture was cooled to 25° C. and quenched by adding water dropwise until effervescence ceased. The mixture was then treated with 10% H$_2$SO$_4$ and stirred at 25° C. for 3 hours. The mixture then was extracted with diethyl ether (2×) and the organic layer was dried (Na$_2$SO$_4$) and the solvent was removed in vacuo. The crude product was purified by flash column chromatography using CH$_2$Cl$_2$:MeOH/10:1 as eluent to provide the desired product [16] (0.0557 g, 57%) as a light yellow oil: $^1$H NMR (500 MHz, CDCl$_3$) δ 7.24 (d, J=17 Hz, 1H), 7.10 (m, 1H), 7.08 (d, J=21.2 Hz, 1H), 4.64 (s, 2H), 3.14 (m, 1H), 2.91 (d, J=18.5 Hz, 1H), 2.68 (m, 2H), 2.47 (m, 1H), 2.31 (m, 1H), 1.92 (m, 6H), 1.34 (m, 3H), 0.84 (d, J=7.1 Hz), 0.50 (m, 2H), 0.11 (m, 2H); Anal. calc. for C$_{19}$H$_{27}$NO: C, 79.95; H, 9.53; N, 4.91. Found: C, 79.70; H, 9.50; N, 4.68.

(±)-3-(Cyclopropylmethyl)-1,2,3,4,5,6-hexahydro-N-hydroxy-cis-6,11-dimethyl-2,6-methano-3-benzazocin-8-carboxamidine [14]. A modification of a known procedure (Jendralla, H.; Seuring, B.; Herchen, J.; Kulitzscher, B.; Wunner, J. *Tetrahedron* 1995, 51, 12047-12068) was used in this preparation. A mixture of (±)-3-(cyclopropylmethyl)-1,2,3,4,5,6-hexahydro-cis-6,11-dimethyl-2,6-methano-3-benzazocin-8-carbonitrile [1] (0.230 g, 0.82 mmol), hydroxylamine hydrochloride (0.100 g, 1.44 mmol) and triethylamine (0.30 mL, 2.15 mmol) in 1 mL of absolute ethanol was stirred at reflux under an argon atmosphere for 5 h. The reaction mixture was concentrated in vacuo and the residue was taken up in 15 mL of CH$_2$Cl$_2$ and washed with water. The organic phase was dried (Na$_2$SO$_4$) and evaporated to give crude product. Flash column chromatography using CH$_2$Cl$_2$:MeOH:NH$_4$OH (conc)/25:1:0.1 provided the desired compound 14 (0.216 g, 84%) as a white foam: $^1$NMR (500 MHz, CDCl$_3$) δ 9.48 (br s, 1H), 7.56 (d, J=1.5 Hz, 1H), 7.33 (dd, J$_1$=1.5 Hz, J$_2$=7.8 Hz, 1H), 7.08 (d, J=7.8 Hz, 1H), 4.84 (s, 2H), 3.19 (m, 1H), 2.94 (d, J=18.8 Hz, 1H), 2.72 (m, 2H), 2.48 (dd, J$_1$=6.3 Hz, J$_2$=12.5 Hz, 1H), 2.34 (dd, J$_1$=6.6 Hz, J$_2$=12.5 Hz, 1H), 2.01 (m, 3H), 1.42 (s, 3H), 1.34 (d, J=11.4 Hz, 1H), 0.92 (m, 1H), 0.84 (d, J=6.8 Hz, 3H), 0.51 (m, 2H), 0.12 (m, 2H); IR (film) ν$_{max}$ 3365, 2921, 1634, 1577 cm$^{-1}$; MS (CI) m/z 314 (M+H)$^+$; Anal. calc. for C$_{19}$H$_{27}$N$_3$O: C, 72.81; H, 8.68; N, 13.47. Found: C, 72.96; H, 8.67; N, 13.18.

(±)-3-(Cyclopropylmethyl)-1,2,3,4,5,6-hexahydro-cis-6,11-dimethyl-2,6-methano-3-benzazocin-8-thiocarboxamide [5]. A modification of a known procedure (Varma R. S.; Kumar, D. Organic Lett. 1999, 1, 697-700) was used in this preparation. A mixture of (±)-3-(cyclopropylmethyl)-1,2,3,4,5,6-hexahydro-cis-6,11-dimethyl-2,6-methano-3-benzazocin-8-carboxamide [4] (0.0298 g, 0.1 mmol) and Lawsson's reagent (0.0320 g, 0.08 mmol) in 1 mL of toluene was sealed in a glass tube under an argon atmosphere. The glass tube was put in a microwave oven and irradiated for 7 min. Additional Lawsson's reagent (0.0160 g, 0.04 mmol) was added and the reactants was allowed to be irradiated for additional 7 min. The reaction mixture was taken up in 10 mL of CH$_2$Cl$_2$ and washed with water. The organic phase was dried with sodium sulfate and evaporated to give crude product. Chromatography on silica gel using CH$_2$Cl$_2$:MeOH:NH$_4$OH (conc)/40:1:0.1 the provided desired compound 5 (0.022 g, 70.1%) as a yellow crystalline solid: mp 171-173° C.; $^1$H NMR (500 MHz, CDCl$_3$) δ 7.78 (d, J=1.9 Hz, 1H), 7.64 (brs, 1H), 7.60 (dd, J$_1$=1.9 Hz, J$_2$=8.1 Hz, 1H), 7.19 (brs, 1H), 7.09 (d, J=8.1 Hz, 1H), 3.16 (m, 1H), 2.95 (d, J=19.0 Hz, 1H), 2.70 (m, 2H), 2.46 (dd, J$_1$=6.1 Hz, J$_2$=12.4 Hz, 1H), 2.32 (dd, J$_1$=6.3 Hz, J$_2$=12.4 Hz, 1H), 1.92 (m, 3H), 1.43 (s, 3H), 1.34 (m, 1H), 0.85 (m, 1H), 0.83 (d, J=7.1 Hz, 3H), 0.51 (m, 2H), 0.10 (m, 2H); IR (film) v. 3172, 2920, 1617, 1424 cm$^{-1}$; MS (CI) m/z 315 (M+H)$^+$; Anal. calc. for C$_{19}$H$_{26}$N$_2$S0.75H$_2$O: C, 69.58; H, 8.45; N, 8.54. Found: C, 69.54; H, 8.15; N, 8.26.

(±)-[3-(Cyclopropylmethyl)-1,2,3,4,5,6,-hexahydro-cis-6,11-dimethyl-2,6-methano-3-benzazocin-8-yl]-methylamine [15]. (±)-3-(Cyclopropylmethyl)-1,2,3,4,5,6-hexahydro-cis-6,11-dimethyl-2,6-methano-3-benzazocin-8-carbonitrile [1] (0.154 g, 0.55 mmol) was dissolved in Et$_2$O (1.1 mL) to obtain a 0.5 M solution. This solution was added dropwise via syringe to a vigorously stirred solution of 1.0 M LiAlH$_4$ in Et$_2$O (1.1 mL, 1.1 mmol) at 0° C. After stirring at room temperature for 10 min, water was added dropwise to quench the reaction. The resulting solution was then extracted with EtOAc several times and the combined EtOAc layers were dried (Na$_2$SO$_4$), and filtered. The solvent was removed in vacuo and the residue purified by flash column chromatography (CH$_2$Cl$_2$:MeOH:Et$_3$N/10:1:0.2) to yield the desired product 15 (0.105 g, 67%) as a brown oil: $^1$H NMR (500 MHz, CDCl3) δ 7.16 (s, 1H), 7.04 (m, 2H), 3.82 (s, 2H), 3.16 (s, 1H), 2.91 (d, J=8.3Hz, 1H), 2.70 (m, 2H), 2.49 (m, 1H), 2.34 (m, 1H), 1.92 (m, 5H), 1.39 (m, 4H), 0.85 (m, 4H), 0.51 (d, J=7.6 Hz, 2H), 0.11 (m, 2H); IR (film)<$_{max}$ 3075, 2962, 2917, 2814, 1574, 1499, 1462, 1428, 1380, 1333, 1218, 1101, 1075, 1018, 963 cm$^{-1}$; Anal. calc. for C$_{19}$H$_{28}$N$_2$0.5H$_2$O: C, 77.77; H, 9.96; N, 9.54. Found: C, 78.18; H, 10.17; N, 9.39.

(±)-N[3-(Cyclopropylmethyl)-1,2,3,4,5,6,-hexahydro-cis-6,11-dimethyl-2,6-methano-3-benzazocin-8-yl]-formamide [19]. A modification of a known procedure (Chakrabarty, M.; Khasnobis, S.; Harigaya, Y.; Kinda, Y. Synthetic Comm. 2000, 30, 187-200.) was used in this preparation. (±)-3-(Cyclopropylmethyl)-1,2,3,4,5,6-hexahydro-cis-6,11-dimethyl-2,6-methano-3-benzazocin-8-amine [37] (0.091 g, 0.337 mmol) was treated with 96% formic acid (20 mL) and was heated at 100° C. for 14 h. The solution was then poured onto crushed ice and basified with solid NaHCO$_3$. The organic material was extracted into EtOAc (3×) and the extracts were washed with water and dried (Na$_2$SO$_4$). After concentration in vacuo, the crude product was purified by flash column chromatography (CH$_2$Cl$_2$:MeOH:NH$_4$OH/10:1:0.05) to yield the desired product 19 as a brown oil (0.065 g, 65%): $^1$H NMR (500 MHz, CDCl$_3$) δ 8.62 (d, J=11.5 Hz, 0.5H, CHO of one rotomer), 8.34 (d, J=1.7 Hz, 0.5H, CHO of other rotomer), 8.17 (d, J=10.5 Hz, 0.5H, NH of one rotomer), 7.57 (br s, 0.5H, NH of other rotomer), 7.36 (m, 1H), 7.04 (m, 1H), 6.89 (m, 1H), 3.15 (m, 1H), 2.90 (m, 1H), 2.72 (m, 2H), 2.47 (m, 1H), 2.32 (m, 1H), 1.95 (m, 3H), 1.32 (m, 4H), 0.85 (m, 4H), 0.51 (m, 2H), 0.11 (m, 2H); IR (film) ν$_{max}$ 3265, 2963, 2922, 1694, 1682, 1614, 1538, 1503, 1462, 1402, 1380, 1311, 1218, 1100, 1074, 1020, 964, 888, 808 cm$^{-1}$; MS (CI) m/z 299 (M+H)$^+$; Anal. calc. for C$_{19}$H$_{26}$N$_2$O0.125H$_2$O: C, 75.90; H, 8.88; N, 9.32. Found: C, 76.00; H, 8.95; N, 9.13.

The remaining compounds of Table 1 were prepared in similar fashion, except Example 8, which was made by the CO/palladium route, but with a slight variation using 2.0 M CH$_3$NH$_2$ in THF, rather than gaseous CH$_3$NH$_2$, and DMF rather than DMSO; mp=155-156° C.; 25.6% yield. 24—[the (±)-8-CONH$_2$ analogue of ethylketocyclazocine (R$^2$ and R$^{2a}$=O; R$^6$=Et)] was made by the nitrile hydrolysis route, mp=194-196° C.; Step 1—89.1%, Step 2—81.4%. 23—[the (±)-8-CONH$_2$ analogue of ketocyclazocine (R$^2$ and R$^{2a}$=O; R$^6$=Me)] was made by the nitrile hydrolysis route, mp=206-207° C.; Step 1—99.7%, Step 2—94.2%. It was also made by the CO/Pd route in 34.7% yield.

In general, the chemistry described above works in the presence of the variety of functional groups found on known core structures. The exceptions would be morphine and congeners having a free 6-OH, which can be protected by a TBDPS (t-butyldiphenylsilyl) group [see Wentland et al J. Med. Chem. 43, 3558-3565 (2000)].

The compound identified as Example 43 in table 4 was prepared by treating the nitrile of nalbuphine with an excess of potassium hydroxide in t-butanol as described for example 4 above. Hydrolysis of the nitrile appears to have proceeded more slowly than elimination and ring opening.

Although this invention is susceptible to embodiment in many different forms, preferred embodiments of the invention have been shown. It should be understood, however, that the present disclosure is to be considered as an exemplification of the principles of this invention and is not intended to limit the invention to the embodiments illustrated. It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genus (I) that are not already in the possession of the public.

I claim:

1. A method of treating a disease or condition selected from pain, pruritus, diarrhea, cough, drug addiction, and irritable bowel syndrome comprising the step of administering to a subject in need thereof a compound of formula:

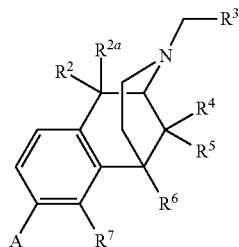

wherein
A is

Y is chosen from O and S;
$R^1$ is —$NHR^8$;
$R^2$ and $R^{2a}$ are both hydrogen or taken together $R^2$ and $R^{2a}$ are =O;
$R^3$ is chosen from hydrogen, lower alkyl, alkenyl, aryl, heterocyclyl, benzyl and hydroxyalkyl;
$R^4$ is chosen from hydrogen, hydroxy, amino, lower alkoxy, $C_1$-$C_{20}$ alkyl and $C_1$-$C_{20}$ alkyl substituted with hydroxy or carbonyl;
$R^5$ is lower alkyl;
$R^6$ is lower alkyl;
$R^7$ is chosen from hydrogen and hydroxy; or together $R^4$, $R^5$, $R^6$ and $R^7$ may form from one to three rings, said rings having optional additional substitution; and,
$R^8$ is hydrogen.

2. The method according to claim 1 wherein:
$R^4$ is chosen from hydrogen, hydroxy, lower alkoxy, $C_1$-$C_{20}$ alkyl and $C_1$-$C_{20}$ alkyl substituted with hydroxy or carbonyl;
$R^5$ is lower alkyl;
$R^6$ is lower alkyl; and
$R^7$ is hydrogen or hydroxy.

3. The method according to claim 2 wherein:
$R^3$ is chosen from hydrogen, cyclopropyl, cyclobutyl, phenyl, vinyl, dimethylvinyl, hydroxycyclopropyl, furanyl, and tetrahydrofuranyl;
$R^4$ is chosen from hydrogen and 3-oxo-5-cyclopentyl-1-pentanyl;
$R^5$ is methyl; and
$R^6$ is methyl or ethyl.

4. The method according to claim 1 wherein together $R^5$, $R^6$ and $R^7$ form two rings, said morphinan having the structure:

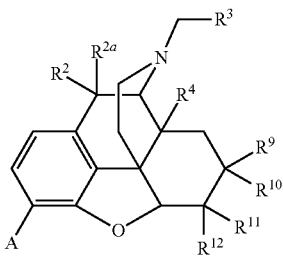

wherein $R^4$ is hydrogen, hydroxy, amino or lower alkoxy;
$R^9$ is hydrogen or lower alkyl;
$R^{10}$ is chosen from hydrogen, lower alkyl and hydroxy (lower alkyl); or together, $R^9$ and $R^{10}$ form a spiro-fused carbocycle of 5 to 10 carbons;
$R^{11}$ is hydrogen;
$R^{12}$ is chosen from hydroxy, lower alkoxy, $NH_2$, —$N(CH_2CH_2Cl)_2$, and —NHC(O)CH=CHCOOCH$_3$; or
together, $R^H$ and $R^{12}$ form a carbonyl or a vinyl substituent; or
together, $R^4$ and $R^H$ form a sixth ring.

5. The method according to claim 4, wherein $R^4$ and $R^H$ form a sixth ring, of formula

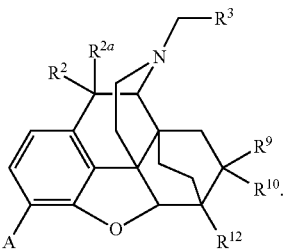

6. The method according to claim 5 wherein
$R^9$ is hydrogen;
$R^{10}$ is hydroxy(lower alkyl); and
$R^{12}$ is lower alkoxy.

7. The method according to claim 4, wherein $R^H$ and $R^{12}$ form a carbonyl substituent, of formula:

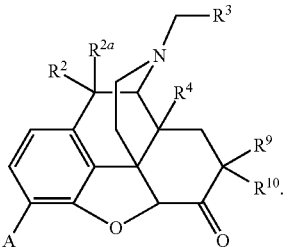

8. The method according to claim 7 wherein
$R^2$ and $R^{2a}$ are both hydrogen;
$R^4$ is chosen from hydrogen, hydroxy, amino and lower alkoxy; and
$R^9$ and $R^{10}$ are both hydrogen or
together, $R^9$ and $R^{10}$ form a spiro-fused carbocycle of 5 to 10 carbons.

9. The method according to claim 8 wherein $R^9$ and $R^{10}$ are both hydrogen.

10. The method according to claim 4, wherein $R^{11}$ and $R^{12}$ form a vinyl substituent, of formula:

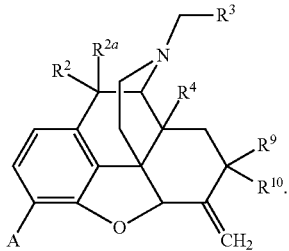

11. The method according to claim 10 wherein
$R^2$ and $R^{2a}$ are both hydrogen;
$R^4$ is hydroxy; and
$R^9$ and $R^{10}$ are both hydrogen.

12. The method according to claim 4 wherein
$R^2$ and $R^{2a}$ are both hydrogen;
$R^4$ is hydroxy;
$R^9$ and $R^{10}$ are both hydrogen; and
$R^{12}$ is chosen from: —NH$_2$, —N(CH$_2$CH$_2$Cl)$_2$, and —NHC(O)CH=CHCOOCH$_3$.

13. The method according to claim 1 wherein together $R^5$, $R^6$ and $R^7$ form two rings of formula:

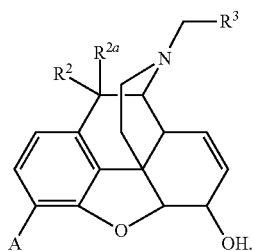

14. The method according to claim 4 wherein $R^4$ and $R^{11}$ form a sixth ring, of formula

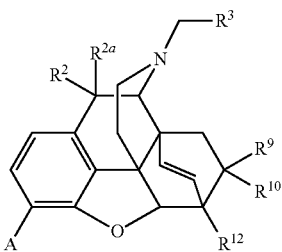

wherein
$R^9$ is hydrogen;
$R^{10}$ is hydroxy(lower alkyl); and
$R^{12}$ is lower alkoxy.

15. A method of treating a disease or condition selected from pain, pruritus, diarrhea, cough, drug addiction, and irritable bowel syndrome, comprising the step of administering a 3-carboxamide substituted morphinan compound to a subject in need thereof.

16. The method of claim 15 wherein the morphinan compound has the formula:

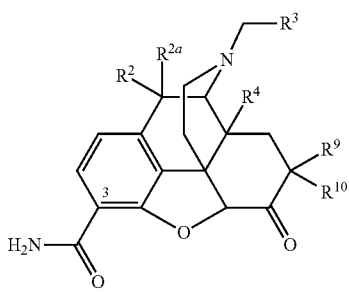

Wherein, $R^2$ and $R^{2a}$ are both hydrogen; R3 is chosen from hydrogen, lower alkyl, alkenyl, aryl, heterocyclyl, benzyl and hydroxyalkyl;
$R^4$ is hydroxyl; and,
$R^9$ and $R^{10}$ are both hydrogen.

17. The method according to claim 15 wherein the drug addiction is heroin, cocaine, nicotine or alcohol addiction.

* * * * *

UNITED STATES PATENT AND TRADEMARK OFFICE
CERTIFICATE OF CORRECTION

PATENT NO. : 8,642,615 B2  Page 1 of 1
APPLICATION NO. : 13/556650
DATED : February 4, 2014
INVENTOR(S) : Mark P. Wentland It is certified that error appears in the above-identified patent and that said Letters Patent is hereby corrected as shown below:

In the Claims

Column 30, Line 22: Claim 4, Delete "$R^H$" and insert -- $R^{11}$ --

Column 30, Line 25: Claim 5, Delete "$R^H$" and insert -- $R^{11}$ --

Column 30, Line 44: Claim 7, Delete "$R^H$" and insert -- $R^{11}$ --

Signed and Sealed this
Twenty-second Day of April, 2014

Michelle K. Lee
*Deputy Director of the United States Patent and Trademark Office*